United States Patent
Shimizu (10) Patent No.: US 9,498,115 B2
(45) Date of Patent: Nov. 22, 2016

(54) OPHTHALMIC MEASUREMENT DEVICE, AND OPHTHALMIC MEASUREMENT SYSTEM EQUIPPED WITH OPHTHALMIC MEASUREMENT DEVICE

(71) Applicant: NIDEK CO., LTD., Gamagori-shi, Aichi (JP)

(72) Inventor: Kazunari Shimizu, Toyokawa (JP)

(73) Assignee: NIDEK CO., LTD., Gamagori-shi (JP)

( * ) Notice: Subject to any disclaimer, the term of this patent is extended or adjusted under 35 U.S.C. 154(b) by 159 days.

(21) Appl. No.: 14/390,279

(22) PCT Filed: Apr. 5, 2013

(86) PCT No.: PCT/JP2013/060538
§ 371 (c)(1),
(2) Date: Oct. 2, 2014

(87) PCT Pub. No.: WO2013/151171
PCT Pub. Date: Oct. 10, 2013

(65) Prior Publication Data
US 2015/0055088 A1    Feb. 26, 2015

(30) Foreign Application Priority Data
Apr. 6, 2012    (JP) ................................ 2012-087715

(51) Int. Cl.
*A61B 3/10*    (2006.01)
*A61B 3/00*    (2006.01)
(Continued)

(52) U.S. Cl.
CPC ........... *A61B 3/0025* (2013.01); *A61B 3/0058* (2013.01); *A61B 3/04* (2013.01); *A61B 3/103* (2013.01); *A61B 3/1015* (2013.01); *A61B 3/12* (2013.01)

(58) Field of Classification Search
CPC   A61B 3/0033; A61B 3/0041; A61B 3/0058; A61B 3/028; A61B 3/0285; A61B 3/036; A61B 3/04; A61B 3/1025; A61B 3/103; A61B 3/1035

USPC ........ 351/205, 206, 210, 227, 237, 241, 246
See application file for complete search history.

(56) References Cited

U.S. PATENT DOCUMENTS

| 5,856,861 A * | 1/1999 | Hosoi ................. A61B 3/0285 351/222 |
| 2002/0140902 A1 | 10/2002 | Guirao et al. |

(Continued)

FOREIGN PATENT DOCUMENTS

| JP | A-10-108837 | 4/1998 |
| JP | A-10-216092 | 8/1998 |

(Continued)

OTHER PUBLICATIONS

International Search Report issued in International Patent Application No. PCT/JP2013/060538 dated May 21, 2013.
(Continued)

*Primary Examiner* — Huy K Mai
(74) *Attorney, Agent, or Firm* — Oliff PLC (57) ABSTRACT

An ophthalmic measurement device to simulate a retinal image of an examinee's eye includes an ocular aberrometer for measuring an aberration of the eye and a calculation control unit for analyzing aberration data obtained by the ocular aberrometer on the naked eye. The calculation control unit calculates subjective correction data intended for a prescription based on a subjective value by obtaining the difference in each meridian direction between a refraction value in the aberration data and a new subjective value of the eye as obtained by a subjective optometry device, obtains a second polynomial equation wherein the coefficient that represents the refraction value among the coefficients of a first polynomial equation used for approximating the aberration data is replaced with a coefficient corresponding to the subjective correction data, back-calculates the aberration data by using the second polynomial equation, and generates a simulation image based on the back-calculated aberration data.

12 Claims, 3 Drawing Sheets

(51) Int. Cl.
*A61B 3/12* (2006.01)
*A61B 3/04* (2006.01)
*A61B 3/103* (2006.01)

(56) References Cited

U.S. PATENT DOCUMENTS

| | | |
|---|---|---|
| 2003/0151721 A1 | 8/2003 | Lai et al. |
| 2004/0263786 A1* | 12/2004 | Williams ............ A61B 3/0025 351/246 |
| 2005/0219461 A1 | 10/2005 | Hirohara |
| 2005/0270490 A1 | 12/2005 | Mihashi et al. |
| 2013/0201447 A1* | 8/2013 | Thompson ............... A61B 3/02 351/201 |

FOREIGN PATENT DOCUMENTS

| | | |
|---|---|---|
| JP | A-2003-47594 | 2/2003 |
| JP | A-2004-105236 | 4/2004 |
| JP | A-2004-510525 | 4/2004 |
| JP | A-2005-516717 | 6/2005 |
| JP | A-2005-211423 | 8/2005 |
| WO | 03/034909 A2 | 5/2003 |
| WO | 2004/096014 A2 | 11/2004 |

OTHER PUBLICATIONS

Nov. 11, 2015 Extended Search Report issued in European Patent Application No. 13772229.4.

* cited by examiner

OPHTHALMIC MEASUREMENT DEVICE, AND OPHTHALMIC MEASUREMENT SYSTEM EQUIPPED WITH OPHTHALMIC MEASUREMENT DEVICE

CROSS-REFERENCE TO RELATED APPLICATIONS

This is a US national phase application based on the PCT International Patent Application No. PCT/JP2013/060538 filed on Apr. 5, 2013, and claiming the priority of Japanese Patent Application No. 2012-087715, filed on Apr. 6, 2012, the entire contents of which are herewith incorporated by reference.

TECHNICAL FIELD

The present invention relates to an ophthalmic measurement device to simulate a retinal image of an examinee's eye, and an ophthalmic measurement system including the ophthalmic measurement device.

BACKGROUND ART

There is known a device configured to project that a spot light beam onto a fundus of an examinee's eye and detect a wavefront information of the light reflected from the fundus by use of a wavefront sensor to measure a wavefront aberration (particularly, a high-order aberration component) of the examinee's eye (see Patent Document 1, for example). There is also known an ophthalmic apparatus configured to project a slit light beam onto a fundus of an examinee's eye and measure a wavefront aberration of the examinee's eye from a phase difference signal when the light reflected from the fundus is detected by a light receiving element (see Patent Document 2, for example).

Based on the thus obtained wavefront aberration data, a retinal image is simulated. However, in the conventional simulation of a retinal image, a point spread function (PSF) is determined from objective wavefront aberration of an examinee's eye, and a simulation image of a predetermined index image is acquired based on the determined PSF and is displayed on a monitor.

There is known an optometric device configured to selectively dispose optical elements such as spherical lenses and cylinder lenses in combination in front of an examinee's eye to present an index in front of the eye, whereby an eye refractive power of the eye is subjectively examined (see Patent Document 3, for example).

[Patent Document 1] JP-A-10 (1998)-216092
[Patent Document 2] JP-A-10 (1998)-108837
[Patent Document 3] JP-A-2005-211423

SUMMARY

Meanwhile, the conventional subjective examination is not always performed in an environment where an examinee actually wears eyeglasses or spectacles. Thus, the examinee could not realize how an index is viewed when he/she wears the eyeglasses. Since the conventional simulation of a retinal image is based on objective data, furthermore, an examinee or an examiner could not estimate how an index is visible at an actual eyeglass prescription value.

The present invention has been made in view of the above conventional arts and has a purpose to provide an ophthalmic measurement device capable of performing good simulation, and an ophthalmic measurement system including the ophthalmic measurement device.

To achieve the above purpose, the invention provides the following configurations. In an ophthalmic measurement device for performing simulation of a retinal image of an examinee's eye, the device including: an ocular aberrometer to measure aberration of the examinee's eye; and a calculation control part configured to analyze aberration data of the examinee's eye without eyeglasses measured by the aberrometer, the calculation control part is configured to: determine a difference in each meridian direction between a refraction value of the aberration data and a new subjective value of the examinee's eye obtained by a subjective optometric device to calculate a subjective correction data intended for a prescription based on a subjective value, and determine a second polynomial by substituting a coefficient corresponding to the subjective correction data for a coefficient representing the refraction value among coefficients of a first polynomial used to approximate the aberration data, back calculate the aberration data by use of the second polynomial, and create a simulation image based on the back-calculated aberration data.

EFFECTS OF THE INVENTION

According to the invention, good simulation can be performed.

MODE FOR CARRYING OUT THE INVENTION

Figure 1:
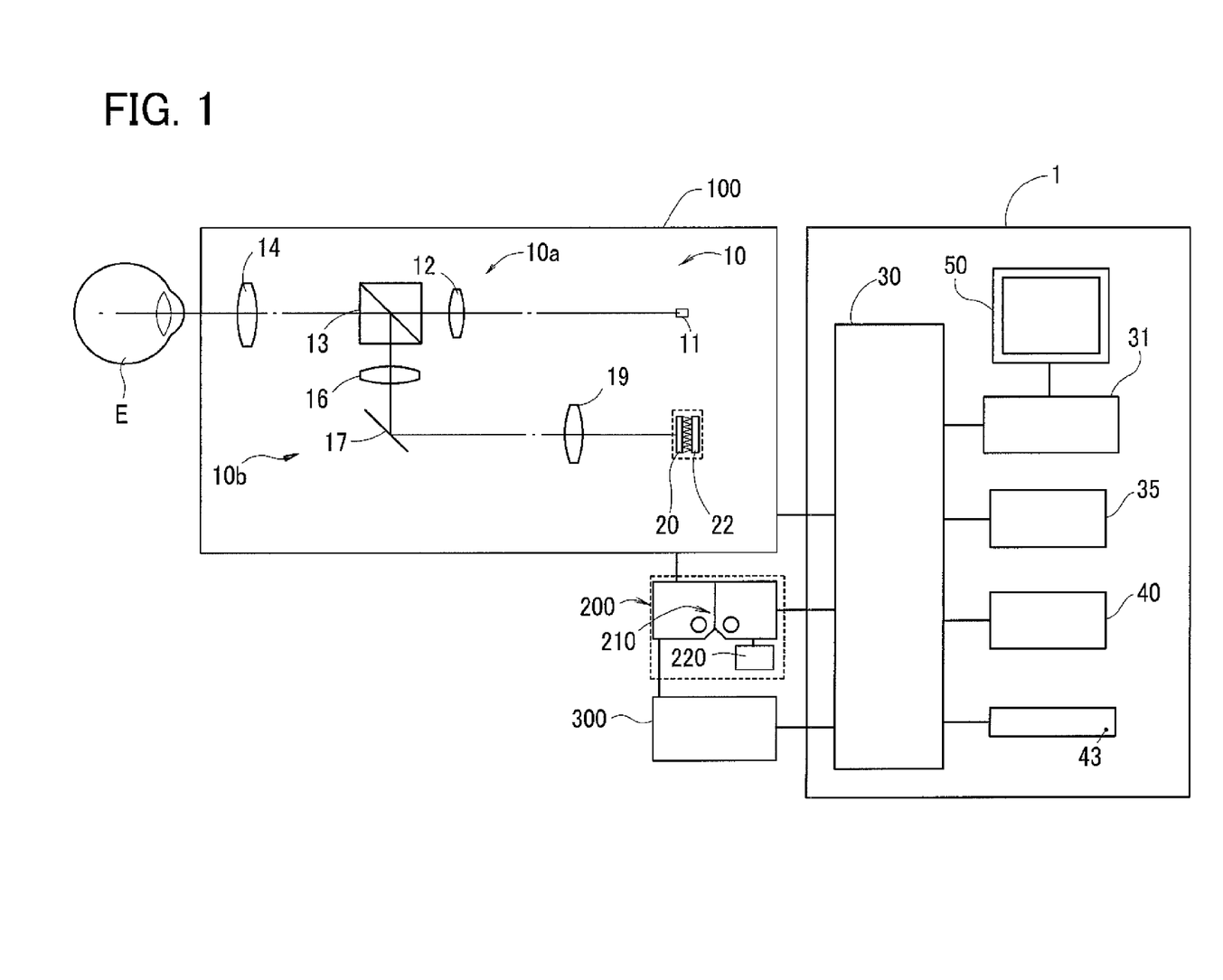
FIG. 1 is a schematic configuration view to explain an optical system and a control system of an ophthalmic measurement device in an embodiment.
Figure 2:
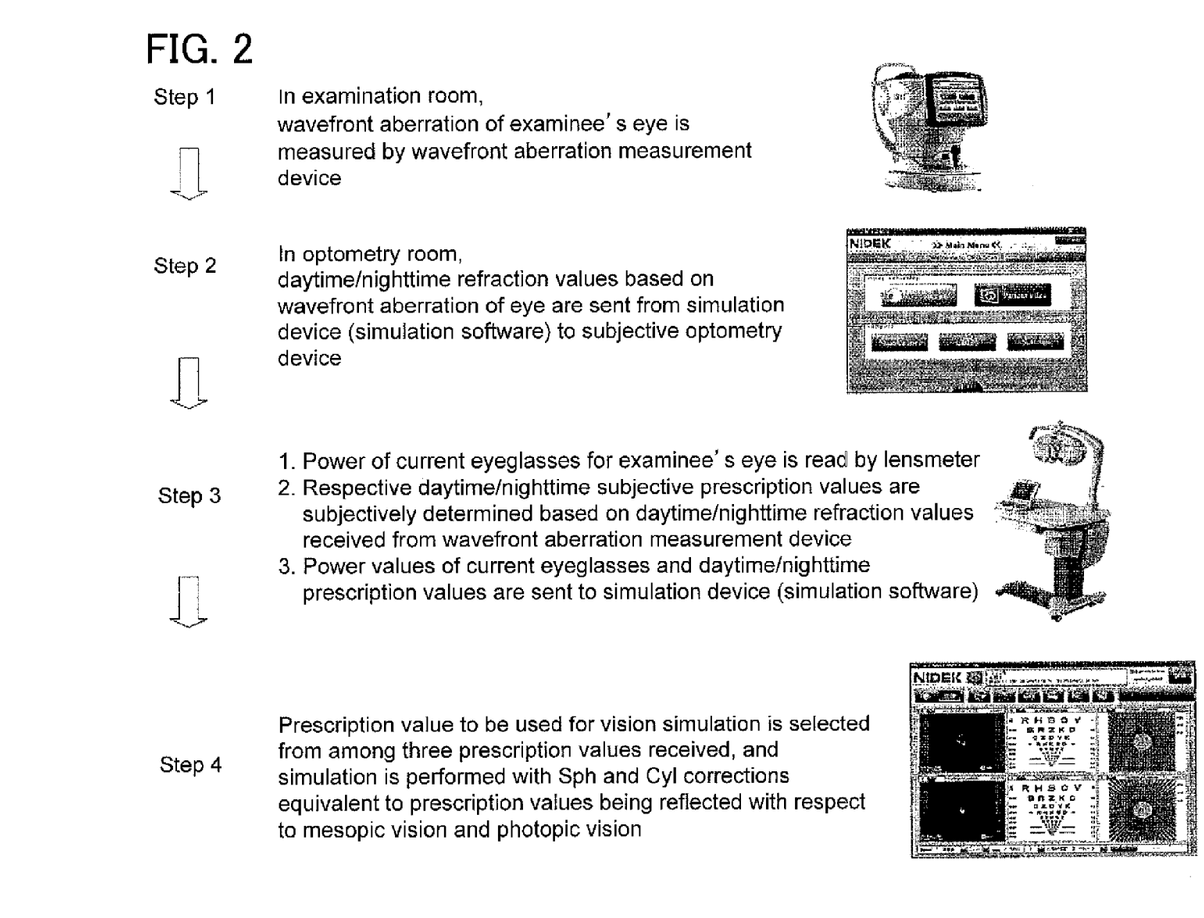
FIG. 2 is a diagram to explain a method of outputting values S, C, and A in the ophthalmic measurement device in the embodiment.

A detailed description of an embodiment of the present invention will now be given referring to the accompanying drawings. FIG. 1 is a block diagram to explain the whole structure of a simulation device (an ophthalmic measurement device) including an ophthalmic measurement program in the present embodiment. FIG. 2 is a flowchart showing one example of the flow of simulation in the present embodiment.

A simulation device 1 is used mainly to simulate a retinal image of an examinee's eye E. This simulation device 1 includes a CPU (a calculation control part) 30, a memory 35, an operation input part (hereinafter, an input part) 40, a printer 43, a monitor 50, an image processing part 31, and others. These parts or units are connected via bus or the like.

The CPU 30 controls operations of the above parts or units based on a retinal image simulation program and various control programs. The input part 40 is an input device to be operated by an examiner. This input part 40 may be selected from a switch, a keyboard, a mouse, a pointing device such as a touch panel, and others. The image processing part 31 is configured to control a display screen of the monitor 50 to display various data, a simulation image, and others. The memory 35 is a storage part to store for example various programs (various control programs for device operation and a retinal image simulation program) to be executed by the CPU 30. The memory 35 serves as a storage device and is selectable from for example a semiconductor memory, a magnetic storage device, and an optical storage device. The monitor 50 serves as an output device and will be controlled by the CPU 30. In the present embodiment, the monitor 50 is a touch panel allowing an examiner to perform input operation and also serves as at least part of the input part 40. The printer 43 prints out a result of the simulation.

In the present embodiment, the CPU 30, input part 40, memory 35, monitor 50, and image processing part 13 may be realized by for example a commercially-available PC (personal computer) that installs therein a retinal image simulation program. This simulation device 1 also may be integrated with at least one of a wavefront aberration measurement device 100, an optometric device 200, and a lens meter 300 which will be described below.

The simulation device 1 is connected to the wavefront aberration measurement device (also referred to as an ocular aberrometer) 100 for measuring a wavefront aberration of the eye E. The wavefront aberration measurement device (hereinafter, the measurement device) 100 includes a measurement optical system configured to project a measurement index onto a fundus of the eye E and receive reflection light of the measurement index from the fundus to measure the wavefront aberration of the eye E.

The measurement device 100 includes a measurement optical system 10 to measure the wavefront aberration of an eye. The measurement optical system 10 includes a light projecting optical system 10a and a light receiving optical system 10b.

The light projecting optical system 10a is configured to project for example a spot-shaped light from a measurement light source onto the fundus of the eye E. The light receiving optical system 10b is configured to split the light beam reflected from the fundus, emerging from the eye E, into a plurality of light beams, which will be received by a two-dimensional light receiving element. The measurement device 100 measures the wavefront aberration of the eye E based on the output from the two-dimensional light receiving element.

To be more concrete, the light projecting optical system 10a includes a measurement light source 11, a relay lens 12, and an objective lens 14 in this order. The measurement light source 11 is placed in a conjugated position with the fundus of the eye E. The light receiving optical system 10b includes, in order from the front of the eye E, the objective lens 14, a half mirror 13, a relay lens 16, a total reflection mirror 17, a collimator lens 19, a microlens array 20, and a two-dimensional light receiving element 22. The light receiving optical system 10b is configured such that a pupil of the eye E and the lens array 20 are in optically substantially conjugate relationship with each other. The microlens array 20 consists of microlenses and a light shielding plate arranged two-dimensionally on a plane perpendicular to a measurement optical axis and used to split the fundus reflection light into the plurality of light beams (JP-A-10 (1998)-216092). The above configuration is configured as a so-called Shack-Hartmann wavefront sensor. As an alternative, a so-called Talbot wavefront sensor may be used in which an orthogonal grid mask is placed in a position conjugated with a pupil, and the light passing through this mask is received by a two-dimensional light receiving element (for the details, see JP-A-2006-149871 filed by the present applicant).

The light emitted from the measurement light source 11 is projected onto the fundus of the eye E via the relay lens 12, the objective lens 14, and the pupil of the eye E. Accordingly, point light images are formed on the fundus of the eye E.

The point light images projected on the fundus of the eye E exit the eye E as reflection beams are collected by the objective lens 14, and then reflected by the half mirror 13. The light reflected by the half mirror 13 is condensed once by the relay lens 16 and then reflected by the total reflection mirror 17. The light reflected by the total reflection mirror 17 passes through the collimator lens 19 and is split into a plurality of light beams by the lens array 20, and then received by the two-dimensional light receiving element 22.

A pattern image received by the two-dimensional light receiving element 22 is stored as image data in the memory 35.

The pattern image varies depending on aberration (low-order aberration, high-order aberration) of the eye E. Accordingly, the pattern image generated by the reflection light from the eye E is analyzed by comparison with a reference pattern image obtained by passage of aberration-free light to determine the wavefront aberration of the eye. Specifically, the measurement device 100 determines a wavefront aberration W $(\rho, \theta)$ based on a deviation amount of dot images of the pattern image.

The measurement device 100 is not limited to the above configuration and may be configured as a well-known one. As another alternative, the measurement device 100 may also be configured to measure a wavefront aberration of an eye E by projecting slit light onto a fundus of the eye E and detecting reflection light through a light receiving element (see JP-A-10 (1998)-108837).

The simulation device 1 and the measurement device 100 are configured as an integral device or separate devices. In the case of the integral device, the CPU 30 controls the measurement optical system 10 and measures the wavefront aberration of an eye based on the data acquired by the measurement optical system 10. The CPU 30 is also used for control-calculation processing in the measurement device 100. In the separate devices, the simulation device 1 and the measurement device 100 are connected via LAN or the like so as to enable transmitting and receiving (communicating) optometric data. Various data (for example, wavefront aberration data of the eye E) obtained by the measurement device 100 are stored in the memory 35.

<Connection to Subjective Optometric Device>

The simulation device 1 is connected to the subjective optometric device (hereinafter, optometric device) 200. This optometric device 200 is used mainly to subjectively measure a refractive power of the eye E. Subjective examination is performed to examine the subjective refractive power by checking whether or not an examinee is able to visually recognize a target presented by a target presenting device or optotypes.

The optometric device 200 is able to transmit and receive (communicate) optometric data to and from the simulation device 1 and the measurement device 100. The optometric device 200 acquires refraction values (objective values expressed by e.g., a spherical power (S), a cylinder power (C), an astigmatic axis angle (A)) based on the wavefront aberration measured by the measurement device 100. The optometric device 200 performs subjective examination as a result of switching of optical characteristics of the electrical elements (sphere lens, cylinder lens, etc.) placed in front of the eye based on the refraction value. The optometric device 200 stores the refraction value acquired by the measurement device 100 into a memory 220. The optometric device 200 stores the power of eyeglasses obtained by the lens meter.

In the subjective examination, the optometric device 200 determines a perfect correction power in order to obtain a best visual acuity of the examinee. Thereafter, the optometric device 200 determines a final subjective value (an eyeglass prescription value) from the perfect correction power according to experiences of an examinee or a predetermined method. The optometric device 200 may be configured to measure a subjective value in a daylight vision (photopic vision) condition and a subjective value in a twilight vision (mesopic vision) condition.

The optometric device 200 includes for example a pair of right and left lens parts 210 disposed in front of the eye E.

Each of the lens parts 210 includes lens disks each of which having various kinds of optical elements (sphere lens, cylinder lens, etc.) concyclically arranged, and a rotation drive part for rotating the lens disks.

The optometric device 200 is not limited to the above configuration. For example, trial frame eyeglasses are included as one component of the optometric device 200. The trial frame eyeglasses are configured to change over an optical element to be placed in the trial frame by examiner's hands.

The optometric device 200 can perform the subjective examination as the changeover of optical characteristics of the optical elements (sphere lens, cylinder lens, etc.) to be placed in front of the eye based on the obtained eyeglass power.

<Connection to Lens Meter>

The simulation device 1 is connected to the lens meter 300. The lens meter 300 is used to measure the powers of eyeglasses currently used by an examinee. An examiner examines the powers of the eyeglasses worn by the examinee by use of the lens meter 300.

The lens meter 300 can transmit and receive (communicate) optometric data to and from the simulation device 1. The lens meter 300 includes a light projecting optical system arranged to project examination light to a lens of the eyeglasses, and a light receiving optical system arranged to receive the examination light having passed through the eyeglass lens through a light receiving element. The lens meter 300 is configured to measure the power of the eyeglasses based on a light receiving signal from the light receiving element. The lens meter 300 may be a lens meter capable of measuring a distribution of eyeglass powers in the form of mapping. As another alternative, the lens meter 300 may also be configured to measure each of the power of eyeglasses for daytime and the power of eyeglasses for nighttime which the examinee possesses.

The power (S, C, A) of each eyeglass lens measured in advance by the lens meter 300 is transferred to the simulation device 1 and used to create a simulation image. This data transfer may be directly made from the lens meter 300 to the simulation device 1 or may be made from the lens meter 300 to the simulation device 1 via the optometric device 200.

FIG. 2 is a flowchart showing an example of vision simulation in the present embodiment.

Briefly, the simulation device 1 performs the vision simulation based on wavefront aberration data of the eye E measured by the measurement device 100 and a subjective value subjectively measured by the optometric device 200.

In step 1, the measurement device 100 measures the wavefront aberration of the eye E. The measurement device 100 is placed in for example an examination room.

In step 2, the simulation device 1 acquires a naked-eye wavefront aberration data of the eye E measured by the measurement device 100. The simulation device 1 is placed in for example an optometry room. The simulation device 1 stores the acquired wavefront aberration data in the memory 35.

The CPU 30 analyzes the wavefront aberration data obtained by the measurement device 100. The CPU 30 further calculates a spherical power (S), an astigmatic power (C), and an astigmatic axis angle (A) based on an obtained wavefront aberration W ($\rho$, $\theta$). For instance, the CPU 30 determines the wavefront aberration data of the eye E in a region corresponding to a predetermined pupil diameter. Then, refraction values (SCA (REF)) of the eye E are determined based on a low-order aberration component calculated from the determined wavefront aberration data.

In the present embodiment, the CPU 30 sets predetermined pupil diameters for daytime (daylight vision) and for nighttime (twilight vision) respectively and outputs a daytime refraction value and a nighttime refraction value. For instance, the CPU 30 adopts $\phi$=4 mm as a predetermined value of the pupil diameter for daytime and $\phi$=6 mm as a predetermined value of the pupil diameter for nighttime.

A method of calculating the objective values (SCA) from the wavefront aberration W ($\rho$, $\theta$) will be briefly explained. The wavefront aberration W ($\rho$, $\theta$) is quantified by application of expansion of the known Zernike polynomial which is one of the polynomials used to approximate the wavefront aberration data.

$$W(\rho,\theta) = \Sigma_{i=0}^{\infty} C_i Z_i \qquad [\text{Eq. 1}]$$

In the equation, $Z_i$ is the i-th one of the Zernike's polynomials, and $C_i$ is a coefficient thereof. $\rho$ indicates a relative position (in a range of 0 to 1) with respect to the pupil diameter and $\theta$ indicates an angle (0 to $2\pi$) measured counterclockwise with respect to an X axis. A standardized display method provides the following expression 2.

$$W(\rho, \theta) = \sum_n \sum_m C_n^m Z_n^m(\rho, \theta) \qquad [\text{Eq. 2}]$$

$$Z_n^m(\rho, \theta) = N_n^m R_n^m(\rho)\cos m\theta; \; 0 \le m - N_n^m R_n^m(\rho)\sin m\theta; \; m < 0$$

$$R_n^m(\rho) = \sum_{s=0}^{(n-|m|)/2} \{(-1)^s (n-s)!/s![0.5(n+|m|)-s]![0.5(n-|m|)-s]!\} \rho^{n-2s}$$

A normalized constant is expressed as below.

$$N_n^m = \sqrt{2(n+1)/(1+\delta_{m0})} \qquad [\text{Eq. 3}]$$

The spherical power (S), astigmatic power (C), and astigmatic axis angle (A) are expressed in the terms of the polynomials of degree 2 or less.

$$S = -4\sqrt{3} \cdot C_2^0 / R^2 \qquad [\text{Eq. 4}]$$

$$C = -4\sqrt{6} \cdot \sqrt{(C_2^{-2})^2 + (C_2^2)^2} \Big/ R^2$$

$$A = \tan^{-1}\left(\frac{C_2^{-2}}{C_2^2}\right) \cdot \frac{1}{2} \cdot \frac{180}{\pi} + 90$$

In the above equations, R is the radius (mm) of a pupil diameter to be analyzed. A high-order aberration component is determined in the terms of the polynomials of degree 3 or higher.

For example, when the wavefront aberration W ($\rho$, $\theta$) is to be determined by using a value of a predetermined pupil diameter P and further the objective values (S, C, A) are determined, R=P/2 is used. The CPU 30 outputs the determined refraction values (SCA (REF)) of the eye E on the monitor 50.

The simulation device 1 transmits the determined refraction values (SCA (REF)) of the eye E to the optometric device 200. As an alternative, it may be arranged to calculate the refraction values of the eye E based on the wavefront aberration by the calculation processing part of the measurement device 100 and transmit the calculated refraction value to the optometric device 200.

In step 3, the power of the current eyeglasses is measured by the lens meter 300. The optometric device 200 measures the subjective values by use of the refraction values.

The optometric device 200 determines the subjective values for daytime and for nighttime respectively by subjective optometry based on the daytime refraction value and the nighttime refraction value transmitted from the simulation device 1 or the measurement device 100. The optometric device 200 transmits the power of the current eyeglasses and the subjective values for daytime/nighttime to the simulation device 1. A measurement result of the lens meter 300 is stored in the memory 220 of the optometric device 200 via an operation input part of the optometric device 200.

In step 4, one prescription value to be used for vision simulation is selected from among three prescription values received. For example, the simulation is implemented by reflecting spherical correction and astigmatic correction corresponding to prescription values with respect to each of the mesopic (twilight) vision and the photopic (daylight) vision.

<Simulation Based on Subjective Value>

The simulation device 1 obtains a new subjective value of the eye E measured by the optometric device 200. The CPU 30 obtains the subjective value measured by the optometric device 200 for example via a communication line. The communication line may be wire communication or wireless communication. The CPU 30 may acquire a subjective value input by the input part 40 operated by the examiner. The CPU 30 obtains for example a subjective value for daytime and a subjective value for nighttime respectively. The CPU 30 stores the obtained subjective values in association with the identification information of the eye E in the memory 35 and also enables readout of those values from the memory 35.

Based on the naked-eye wavefront aberration data measured by the measurement device 100 and the subjective values measured by the optometric device 200, the simulation device 1 calculates the wavefront aberration data intended for the correction based on the subjective value.

Specifically, the CPU 30 determines a difference in each meridian direction between the refraction value of the naked-eye wavefront aberration data and the subjective value to calculate the subjective correction data (SCA correction) intended for the prescription based on the subjective values (Correction data=Refraction value based on wavefront aberration−Subjective value). The CPU 30 substitutes a coefficient corresponding to the subjective correction data for a coefficient representing a refraction value of a naked eye among coefficients of the polynomial used to approximate the naked-eye wavefront aberration data. The CPU 30 back calculates the wavefront aberration data by use of the substituted polynomial. The CPU 30 creates a subjective simulation image based on the back-calculated wavefront aberration data. A typical one of the polynomials used to approximate the wavefront aberration data is the Zernike polynomial. The polynomials are not limited thereto and may be any one of the expressions used to approximate the wavefront aberration.

To be concrete, the CPU 30 respectively converts the refraction values and the subjective values to approximate curves (approximate curves representing distribution of eye refractive power (D) in each of the meridian directions (θ)) to determine a difference between the approximate curve of the refraction value and the approximate curve of the subjective value. The CPU 30 calculates a subjective correction data (SCA correction) based on the determined difference in approximate curve. The approximate curve is expressed for example as a sin curve.

The CPU 30 substitutes the correction data (SCA correction) based on the subjective values for the values S, C, and A of quadratic expressions of the Zernike polynomial. The CPU 30 calculates coefficients of the quadratic expression based on the correction data (SCA correction) on the basis of the subjective values.

the CPU 30 substitutes the calculated coefficient of the quadratic expression based on the correction data (SCA correction) on the basis of the subjective values for the coefficient of the quadratic expression with the naked eye among the naked-eye coefficients of the Zernike's polynomial. The CPU 30 back calculates the wavefront aberration data by use of the Zernike's polynomial with the substituted coefficient. The CPU 30 determines the point spread function (PSF) by utilizing the wavefront aberration data calculated by the back calculation.

In the present embodiment, the CPU 30 determines the point image intensity distribution intended for daytime with the prescription based on the subjective value for daytime by use of the wavefront aberration data of the naked eye corresponding to the pupil diameter for daytime and the daytime subjective value. The CPU 30 determines the point image intensity distribution intended for nighttime with the prescription based on the subjective value for daytime using the wavefront aberration data of the naked eye corresponding to the pupil diameter for nighttime and the daytime subjective value. The CPU 30 determines the point image intensity distribution intended for daytime with the prescription based on the subjective value for nighttime using the wavefront aberration data of the naked eye corresponding to the pupil diameter for daytime and the nighttime subjective value. The CPU 30 determines the point image intensity distribution intended for nighttime with the prescription based on the subjective value for nighttime using the wavefront aberration data of the naked eye corresponding to the pupil diameter for nighttime and the nighttime subjective value. It is to be noted that the point image intensity distribution to be calculated may be arbitrarily selected from above.

The CPU 30 makes image processing (convolution integration) of the obtained PSF and the predetermined index (e.g., ETDRS target, resolution chart, and landscape chart). Accordingly, the CPU 30 can obtain a simulation image(s). The simulation image shows how a predetermined target is formed on a retinal plane of the eye E when a prescription for the eye E is prepared with the subjective values. In other words, the CPU 30 obtains the simulation image(s) related to the subjective values measured by the optometric device 200.

In the present embodiment, the CPU 30 performs the image processing to construct the simulation image representing how a predetermined target is visible in the daylight vision and the twilight vision under the prescription for the eye E with the subjective values. To be more specific, the CPU 30 respectively obtains the simulation images in daylight vision and in twilight vision when the prescription for the eye E is prepared with the subjective values for daytime, and the simulation images in daylight vision and in twilight vision when the prescription for the eye E is prepared with the subjective values for nighttime. As an alternative, the CPU 30 may obtain the simulation image in daylight vision when the prescription for the eye E is prepared with the subjective values for daytime and the simulation image in twilight vision when the prescription for the eye E is prepared with the subjective values for nighttime.

The CPU 30 displays the simulation image(s) obtained as above on the monitor 50 via the image processing part 31. In FIG. 2, the CPU 30 displays the PSF image, ETDRS target, and resolution chart side by side (in parallel).

<Simulation Corresponding to Custom Lens>

A conventional eyeglass prescription is prepared corresponding to a 0.25 D step based on subjective values calculated in steps of 0.25 D. In recent years, an eyeglass lens corresponding to smaller steps than 0.25 D (e.g., steps of 0.12, steps of 0.01) is proposed. This demands more detailed eyeglass prescription. As such an eyeglass lens, for example, a free-form lens the power of which is settable in steps of 0.01 is proposed. In this case, the subjective value is calculated in steps smaller than 0.25 D and a lens corresponding to the calculated subjective value is prescribed.

The CPU 30 may be arranged to obtain a first simulation image created by the prescription for the eye E with a first subjective value calculated in steps smaller than 0.25 D and a second simulation image created by the prescription for the eye E with a second subjective value calculated in steps of 0.25 D or more. It is to be noted that the CPU 30 obtains the second subjective value by converting the first subjective value to a step of 0.25 D or more. The optometric device 200 may be arranged to perform in advance the process of converting the first subjective value to the second subjective value. The first subjective value and the second subjective value may be calculated separately by subjective examination. A method of obtaining a simulation image after the subjective values are obtained is the same as above and is not repeatedly explained hereinbelow.

The CPU 30 displays the simulation image(s) obtained as above on the monitor 50 via the image processing part 31. The CPU 30 displays for example the first simulation image and the second simulation image side by side. Alternatively, the CPU 30 selectively displays the first simulation image or the second simulation image.

In the above way, the examiner and the examinee can easily compare a result of a prescription for an eyeglass lens corresponding to smaller steps than 0.25 D and a result of a prescription for a normal lens. Accordingly, the examiner can make the examinee easily recognize merits by wearing of eyeglass lenses corresponding to smaller steps than 0.25 D.

The first subjective value may be a subjective value calculated under the condition that at least one of a S value and a C value is calculated in steps smaller than 0.25 D. The CPU 30 can appropriately obtain the simulation image based on the subjective values in which only the S value is calculated in steps smaller than 0.25 D, the simulation image based on the subjective value in which only the C value is calculated in steps of smaller than 0.25 D, and the simulation image based on the subjective value in which both the S value and the C value are calculated in steps of smaller than 0.25 D. The CPU 30 displays those simulation images selectively or side by side on the monitor 50.

<Simulation Based on Previous Eyeglass Data>

Generally, the simulation device 1 performs vision simulation based on the wavefront aberration data of the eye E objectively measured by the measurement device 100 and the lens power values of the eyeglasses measured by the lens mete 300.

Specifically, the simulation device 1 obtains the lens power values of the current eyeglasses of the examinee measured by the lens meter 300. The simulation device 1 stores the obtained lens power in the memory 35.

The CPU 30 obtains the lens power values of the eyeglasses measured by the lens meter 300 for example through a communication line. This communication line may be wire communication or wireless communication. The CPU 30 may obtain the lens power values of the eyeglasses input on the input part 40 operated by the examiner. The CPU 30 stores the obtained power values of the eyeglasses in association with the identification information of the eye E in the memory 220 and also enables readout of the values from the memory 220.

Next, the simulation device 1 calculates the wavefront aberration data intended for the correction based on the lens power value on the basis of the wavefront aberration data measured by the measurement device 100 and the lens power value of the eyeglasses measured by the lens meter 300.

The CPU 30 determines a difference in each meridian direction between the refraction values of the naked-eye wavefront aberration data and the power values of the eyeglasses. The CPU 30 finds the difference to calculate the eyeglass correction data (SCA eyeglass) intended for wearing of the current eyeglasses (Correction Data=Objective Value−Lens Power Value). Among the coefficients of the polynomial used to approximate the naked-eye wavefront aberration data of the eye E, the CPU 30 substitutes a coefficient corresponding to the eyeglass correction data for the coefficient representing the refraction value of the naked-eye. The CPU 30 back calculates the wavefront aberration data by use of the substituted polynomial and creates the eyeglass simulation image based on the back-calculated wavefront aberration data.

To be concrete, the CPU 30 converts the refraction value and the lens power value to respective approximate curves (approximate curves representing a distribution of eye refractive power (D) in each of the meridian directions ($\theta$)), and determines a difference in approximate curve between the refraction value and the lens power value. The CPU 30 calculates a correction data (SCA correction) based on the calculated difference in approximate curve. The approximate curve is expressed for example as a sin curve.

The CPU 30 substitutes the correction data (SCA eyeglass) based on the lens prescription values for the values S, C, and A of the quadratic expressions of the Zernike polynomial. The CPU 30 calculates a coefficient of the quadratic expression based on the correction data (SCA eyeglass) on the basis of the lens power values.

The CPU 30 substitutes the coefficient calculated based on the correction data (SCA eyeglass) on the basis of the lens power values for the coefficient of the quadratic expression for naked eye among the naked-eye coefficients of the Zernike's polynomial. The CPU 30 back calculates the wavefront aberration data by using the substituted Zernike coefficient. The CPU 30 determines the point spread function (PSF) by utilizing the wavefront aberration data calculated by back calculation.

In the present embodiment, the CPU 30 determines the point image intensity distribution intended for wearing of the current eyeglasses in daytime by using the naked-eye wavefront aberration data corresponding to the pupil diameter for daytime and the lens power values of the eyeglasses. On the other hand, the CPU 30 determines the point image intensity distribution intended for the wearing of the current eyeglasses in nighttime by using the naked-eye wavefront aberration data corresponding to the pupil diameter for nighttime and the lens power values of the eyeglasses.

Next, the CPU 30 performs image processing (convolution integration) of the obtained PSF and the predetermined index (e.g., ETDRS target, resolution chart, landscape chart). Accordingly, the CPU 30 can obtain the simulation mage(s). The simulation image is a simulation image showing how a predetermined target is formed on a retinal plane of the eye E when the prescription for the eye E is prepared with the lens power value.

The CPU 30 obtains the simulation image(s) related to the lens power values measured by the lens meter 300. In the present embodiment, the CPU 30 performs the image processing to construct the simulation image representing how a predetermined target is visible in the daylight vision and the twilight vision under the prescription for the eye E with the lens power values of the eyeglasses.

The CPU 30 displays the simulation image(s) obtained as above on the monitor 50 via the image processing part 31. In FIG. 2, the CPU 30 displays the PSF image, the ETDRS image, and the resolution image side by side.

In the above vision simulation, the space frequency characteristics MTF may be displayed (e.g., in a graph with a lateral axis representing space frequency and a vertical axis representing contrast sensitivity). MTF can be determined by Fourier conversion of PSF obtained from the wavefront aberration of the eye E. This enables more accurate vision simulation.

<Selective Displaying Simulation Image Based on Subjective Values and Simulation Image Based on Previous Eyeglass Data, and Parallel Display>

The CPU 30 receives an operation input signal to select the simulation image(s) to be displayed on the monitor from among the subjective simulation image based on the subjective value for daytime, the subjective simulation image based on the subjective value for nighttime, the eyeglass simulation image based on eyeglass power values, and the naked-eye simulation image based on the naked-eye wavefront aberration (selection step). The CPU 30 displays the selected simulation image on the monitor 50.

Figure 3:
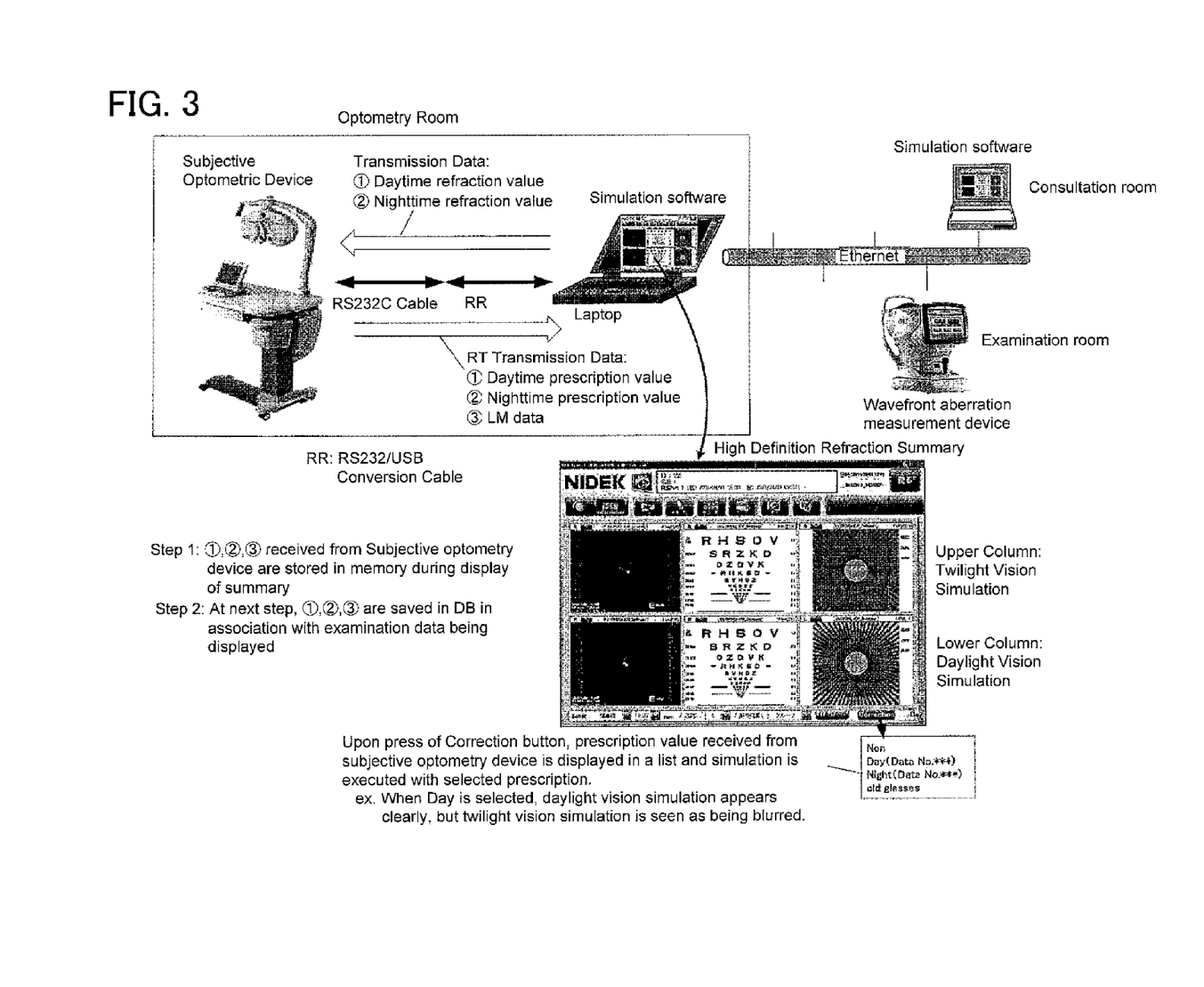
FIG. 3 shows one example of a connection configuration and a flow of data between devices during simulation and one example of a display screen on which an obtained simulation image is displayed in the present embodiment.

FIG. 3 shows one example of the connection configuration and a flow of data between the devices whereby the simulation is performed and also shows one example of a display screen on which the obtained simulation image(s) is displayed in the present embodiment. When a Correction button appearing on the monitor 50 is pressed, the CPU 30 displays prescription values obtained in the optometric device 200 in the form of a list and displays the simulation image(s) related to the selected prescription values. The list selectively displays naked-eye data with no prescription, subjective values for daytime, subjective values for nighttime, and power values of the eyeglasses. The CPU 30 displays side by side the twilight vision simulation image and the daylight vision simulation image corresponding to the selected prescription values. For example, when the subjective values for daytime are selected, the daylight vision simulation image is clearly visible but the twilight vision simulation image is seen as being blurred. An examinee who looks at this image can easily recognize the necessity of the prescription for nighttime. When the subjective values for nighttime are selected, furthermore, the twilight vision simulation image is viewed clearly, but the daylight simulation image is seen as being blurred. Accordingly, an examinee who looks at this image can further recognize the necessity of the prescription for nighttime. When the eyeglass power value is selected, there may be a case where the daylight simulation image and the twilight simulation image is seen as being blurred. An examinee who looks at this image can easily recognize the necessity of new eyeglasses.

The CPU 30 may display, side by side, at least two of the simulation images of the prescription values (naked-eye data with no prescription, subjective value for daytime, subjective value for nighttime, and eyeglass power value (eyeglass prescription value)). By parallel display of the naked-eye data and the simulation image with the subjective values (for daytime and/or nighttime), the examinee can easily recognize a difference in image between the naked-eye state (the state without eyeglasses) and the state with subjective prescription. Thus, particularly an examinee who has not worn eyeglass lenses before can easily recognize the necessity to wear eyeglasses.

By parallel displaying the eyeglass power data and the simulation image with the subjective values (for daytime and/or nighttime), an examinee can easily recognize a difference in image between a state using current eyeglasses and a state with a subjective prescription. Thus, particularly an examinee can easily recognize the necessity to wear new eyeglasses.

By parallel display of the twilight vision simulation images with the subjective value for daytime and the subjective value for nighttime, it is possible to easily recognize a difference in image in twilight vision between the prescription for daytime and the prescription for nighttime. This can make particularly an examinee easily recognize the necessity to wear eyeglasses for nighttime.

REFERENCE SIGNS LIST

50 Display monitor
10 Wavefront aberration measurement optical system
30 Observation optical system
32 Two-dimensional imaging element
70 Control part

The invention claimed is:

1. An ophthalmic measurement device for performing simulation of a retinal image of an examinee's eye, the device comprising:
   an ocular aberrometer to measure aberration of the examinee's eye; and
   a calculation control part configured to:
      analyze aberration data of the examinee's eye without eyeglasses measured by the aberrometer,
      determine a difference in each meridian direction between a refraction value of the aberration data and a new subjective value of the examinee's eye obtained by a subjective optometric device to calculate a subjective correction data intended for a prescription based on a subjective value, and
      determine a second polynomial by substituting a coefficient corresponding to the subjective correction data for a coefficient representing the refraction value among coefficients of a first polynomial used to approximate the aberration data, back calculate the aberration data by use of the second polynomial, and create a simulation image based on the back-calculated aberration data.

2. The ophthalmic measurement device according to claim 1, wherein the calculation control part is further configured to:

determine a difference in each meridian direction between the refraction value and a power value of eyeglasses obtained by a lens meter to calculate eyeglass correction data intended for wearing of the eyeglasses, and determine a third polynomial by substituting a coefficient corresponding to the eyeglass correction data for the coefficient representing the refraction value among the first polynomial used to approximate the aberration data, back calculate the aberration data by use of the third polynomial, and create a simulation image based on the back-calculated aberration data.

3. The ophthalmic measurement device according to claim 2, wherein the calculation control part is further configured to store the subjective value or the power value of the eyeglasses in a storage part in association with identification information of the examinee's eye and enable readout of the subjective value or the eyeglass power value from the storage part.

4. The ophthalmic measurement device according to claim 2, wherein the calculation control part is further configured to display the created simulation image on a monitor.

5. The ophthalmic measurement device according to claim 4, wherein the calculation control part is further configured to:

receive an operation input signal to select the simulation image to be displayed on the monitor from among a simulation image based on the subjective value, a simulation image based on the power value of the eyeglasses, and a simulation image based on aberration data for the naked eye, and display the simulation image on the monitor based on the received operation input signal.

6. The ophthalmic measurement device according to claim 4, wherein the calculation control part is further configured to display the simulation image based on the subjective value and the simulation image based on the power value of the eyeglasses side by side on the monitor.

7. The ophthalmic measurement device according to claim 1, wherein the calculation control part is further configured to obtain each of a subjective value for daytime and a subjective value for nighttime as the subjective value.

8. The ophthalmic measurement device according to claim 1, wherein the calculation control part is further configured to obtain each of a first subjective value which is the subjective value calculated in steps smaller than 0.25 D and a second subjective value which is the subjective value calculated in steps equal to or larger than 0.25 D.

9. The ophthalmic measurement device according to claim 8, wherein the calculation control part is further configured to display a simulation image based on the first subjective value and a simulation image based on the second subjective value selectively or side by side on the monitor.

10. An ophthalmic measurement system comprising:

the ophthalmic measurement device according to claim 1;

a subjective optometric device including an optical element to be placed in front of an examinee's eye and a changeover unit to change optical characteristics of the optical element, the optometric device being configured to measure a new subjective value of the examinee's eye; and a data communication part to communicate optometric data, wherein the calculation control part is further configured to obtain, through the data communication part, the subjective value measured by the subjective optometric device.

11. The ophthalmic measurement system according to claim 10, further comprising:

a lens meter for measuring a power value of eyeglasses, wherein the calculation control part is further configured to obtain, through the data communication part, a power value of current eyeglasses measured by the lens meter.

12. An ophthalmic measurement device for performing simulation of a retinal image of an examinee's eye, the device comprising:

an ocular aberrometer to measure aberration of the examinee's eye; and a calculation control part configured to:

analyze aberration data of the examinee's eye without eyeglasses measured by the aberrometer, determine a difference in each meridian direction between a refraction value of the aberration data and a power value of eyeglasses obtained by a lens meter to calculate eyeglass correction data intended for wearing of the eyeglasses, and determine a second polynomial by substituting a coefficient corresponding to the eyeglass correction data for the coefficient representing the refraction value among a first polynomial used to approximate the aberration data, back calculate the aberration data by use of the second polynomial, and create a simulation image based on the back-calculated aberration data.

* * * * *